United States Patent [19]

Patnoi et al.

[11] 4,214,590
[45] Jul. 29, 1980

[54] METHOD AND APPARATUS FOR PROCESSING AND DISPLAYING DATA IN COMPRESSED FORM

[75] Inventors: Charles M. Patnoi, Golden; Daniel Cooper, Denver; Robert D. Zellers, Lakewood, all of Colo.

[73] Assignee: International Medical Corporation, Englewood, Colo.

[21] Appl. No.: 855,210

[22] Filed: Nov. 28, 1977

[51] Int. Cl.² ............................................. A61B 5/04
[52] U.S. Cl. ............................. 128/710; 346/33 ME; 346/136
[58] Field of Search ...................... 128/2.06 G, 2.06 A, 128/2.06 R, 710; 346/33 ME, 118, 136

[56] References Cited

U.S. PATENT DOCUMENTS

| 3,082,970 | 3/1963 | Rasmussen | 128/2.06 G |
|---|---|---|---|
| 3,111,656 | 11/1963 | Barrett et al. | 346/136 |
| 3,302,639 | 2/1967 | Koffler | 128/2.06 G |
| 3,779,237 | 12/1973 | Goeltz et al. | 128/2.06 A |
| 3,893,453 | 7/1975 | Goldberg et al. | 128/2.06 G |
| 3,922,686 | 11/1975 | France et al. | 128/2.06 G |
| 3,934,267 | 1/1976 | Kosaka et al. | 128/2.06 G |
| 3,951,135 | 4/1976 | Goldberg et al. | 128/2.06 G |
| 3,958,563 | 5/1976 | Fernandez et al. | 346/33 ME |
| 3,986,496 | 10/1976 | Brastad | 128/2.06 R |
| 4,006,737 | 2/1977 | Cherry | 128/2.06 G |
| 4,051,482 | 9/1977 | Andresen | 128/2.06 G |

Primary Examiner—William E. Kamm
Attorney, Agent, or Firm—John E. Reilly

[57] ABSTRACT

A method and apparatus for processing and displaying ECG waveforms and the like is comprised of a playback circuit to demodulate FM and digital signals for transcription on an endless paper loop in a series of straight lines or traces. A paper loop drive unit is capable of handling and advancing the endless loop continuously past one or more scribing pens which are offset in succession to produce a predetermined number of traces in parallel rows across the length of the loop with time segment markings closely correlated with the information recorded.

12 Claims, 5 Drawing Figures

METHOD AND APPARATUS FOR PROCESSING AND DISPLAYING DATA IN COMPRESSED FORM

This invention relates to a novel and improved method and means for processing and displaying physiological data in compressed form and more particularly relates to a method and apparatus for processing and displaying electrocardiograms (ECG) signals in a rapid, dependable and highly efficient manner.

BACKGROUND OF THE INVENTION

Various techniques and systems have been devised for the long term monitoring and displaying of ECG signals. Such systems have become particularly important in permitting the diagnostician to monitor many of the transient cardiac abnormalities of an ambulant patient as he pursues his normal day-to-day activities. It is customary to record these activities by means of a portable tape recorder which receives the vital sign data from electrodes attached to different parts of the body so that either a continuous, or a series of periodic, recordings may be made under the control of the patient over an extended time period, for example, on the order of two hours. The electrical signals generated by the heart then may be converted by suitable electronics into a modulated signal in the form of an FM signal which can be recorded on magnetic tape. It will be appreciated that the recording may consist of periods or intervals of somewhat continuous recording if the tape recorder is merely permitted to run; or may consist of a series of short recordings made either at preselected time intervals during the day or at any time that the patient believes it important to record heart activity such as when periods of abnormal heart activity or stress situations are experienced. However, it is highly desirable that the actual playback and processing of such recordings be accomplished in a minimum of time while enabling display of the information within the smallest possible area; yet it is equally as important that the information be compressed and displayed in such a manner as to be presented accurately and clearly for the physician or other diagnostician so that those recording segments of particular interest may be readily perceived.

In the past such information has been displayed by advancing chart recording paper from a continuous roll past one or more scribing pens which receive the ECG signals from a playback circuit and form traces of the waveforms on the paper by deflecting the pens in a direction transversely of the movement of the paper past the pen. When this information is played back in real time, the resultant display over an extended length of the chart recording medium or paper makes it very time-consuming and difficult for the diagnostician to properly review and analyze the results.

Accordingly, various systems and techniques have been devised for overcoming the above and other problems associated with the processing and display of ECG and other vital signs data. For instance, there is disclosed in U.S. Letters Pat. No. 3,958,563 to Fernandez a two-speed recording system in which recording is accelerated during those periods in which the data is of little value by multiplying the speed of advancement of the paper itself past a scribing pen. In U.S. Letters Pat. No. 3,779,237 to Goeltz et al, it is proposed to process long term periods of activity by recording waveforms of the heart in greater than real time and of selectively recording the data of particular interest. Further in U.S. Letters Pat. No. 3,893,453 to Goldberg et al ECG waveforms are displayed on a closed loop of chart recording paper by causing the scribing pen to traverse the entire width of the paper as it is advanced past the pen and accelerating the rate of playback of the information. As a result, the information is displayed in somewhat helical fashion along the entire length of the endless loop. Nevertheless, there is a need and a continuing demand for a system and technique which will permit compressed data recording or transcription of ECG signals in such a way as to be accurately correlated and broken down with respect to time, will facilitate ease of evaluation and diagnosis at maximum efficiency and minimum cost; and further will enable the diagnostician to pinpoint specific segments of interest for playback in a real time format onto a separate chart recording strip or roll. Moreover, notwithstanding continuous playback at a greatly increased rate of speed on the order of ten times the real time recording, important segments such as the cardiac cycle as generally designated by the QRS complex will be sensed and in effect stretched while preserving the amplitude of the waveforms for clarity and accuracy of evaluation.

SUMMARY OF THE THE INVENTION

It is therefore an object of the present invention to provide for a novel and improved method and means for processing data and displaying graphic representations of same in a rapid, dependable manner.

It is another object of the present invention to provide a novel and improved ECG recording medium to facilitate the recording and display of traces of ECG waveforms in a line-over-line manner in which the traces run lengthwise of an endless loop or roll and are accurately correlated with respect to time.

It is another object of the present invention to provide for a novel and improved paper drive system for advancing an elongated paper loop at a constant rate of speed and under constant tension past one or more scribing pens without danger of shifting or misalignment of the paper as it undergoes a series of revolutions past the scribing pens.

It is a further object of the present invention to provide an improved system for loading and handling an ECG recording medium in the form of an endless loop for continuous movement past one or more scribing pens; and further wherein a drive system of the type described is particularly adaptable for use in cooperation with a compressed data playback system to facilitate graphical representation of information recorded over extended time periods.

It is a still further object of the present invention to provide for a novel and improved method and means for playing back ECG signals continuously at a rate of speed many times the real time format for graphical representation on a recording medium while accurately portraying such information both with respect to time and conditions under which the signals were recorded.

It is an additional object of the present invention to present discontinuous traces of ECG signals and like information recorded over an extended time period wherein such traces are presented in hard copy form in a line-over-line manner together with summaries or histograms of the information presented in each trace.

The compressed data recording method and system of the present invention may be best exemplified by describing its use and application for the graphical representation of ECG signals recorded over an extended time period; such as for instance, the monitoring of an ambulatory patient over an extended time period. In accordance with well-known practice, the ECG signals detected may be converted into an FM signal which includes a time or event code correlated with the ECG signal and simultaneously recorded on a magnetic tape or other suitable recording surface. Although not restricted for application to an ambulatory patient, typically the modulated signals are generated in a portable tape recorder onto a tape cassette. The recorded tape may then be inserted into a playback tape deck and, under the control of a microprocessor, the signals are played back and demodulated at a greatly increased rate of speed as they are converted into low voltage analog signals. In this way actual information recorded is compressed when played back and transferred onto a chart recorder. In accordance with the present invention, one or more recording pens are positioned across the width of an endless chart or loop in the chart recorder unit, each pen in succession being capable of recording a trace of information lengthwise of the writing surface on the loop as the loop is continuously advanced across the pen, following which the pen is offset or shifted in preparation for transcribing the next trace in succession starting at a point aligned with the starting point of the first trace. Assuming that the rate of playback speed is increased by a multiple of ten over real time, each ten-second interval of information actually recorded is transcribed in one second on the writing surface. In this relation, the playback circuit will record along the length of the writing surface the time segment markings representing discrete time intervals over which the information is recorded; whereas markings extending across the width of the chart are provided to graphically represent the real time recording intervals and specifically the aggregate of the time intervals over which recordings of the traces were made. In addition, the playback circuit will record at the end of each trace a histogram of heart rate interval and of S-T level which is calculated and stored by a microprocessor as the recording proceeds along each track and then is recorded at the end of each track as a preliminary to shifting of the pen for transcribing the next trace in succession. The microprocessor will also sense and correlate the rate of recording with an internal timer and make any necessary compensation in tape transport motor speed to insure that the rate of playback and recording on the chart are properly aligned with the time segment markings on the chart.

Where a plurality of write heads or scribing pens are employed, each pen is aligned with a different sector or channel of the recording paper and each being activated in succession to transcribe a series of parallel, coextensive traces along the length of the paper until its respective sector or channel is filled whereupon the next pen in succession is activated to record the next series of traces in the same manner until the entire recording is transcribed. Segments of particular interest can be marked on the paper and readily coded into the microprocessor by means of the time segment markings extending lengthwise and transversely of the paper. These segments then may be played back in a real time format onto a separate strip of recording paper. Further, in order to serve as an aid to the diagnostician in evaluation of the initial recording, a pulse stretcher is employed in the playback circuit to in effect elongate or slew the waveforms of the QRS complex in time without affecting the rest of the waveform.

Another feature of the present invention resides in the chart loop support and drive system where, in place of the conventional drum or roll, an extended loop is trained over a stationary bar immediately beneath the scribing pens and its opposite end is passed over a suspension weight roller, there being an intermediate drive roller which cooperates with a pinch roller and a tension roller in driving the paper at a predetermined speed and preselected tension past the scribing pens. The loop suspension and drive system will permit its use in combination with a platen or other flat surface directly downstream of the writing pens so as to permit review and marking on the paper by the diagnostician as the transcription proceeds.

BRIEF DESCRIPTION OF THE DRAWINGS

Other objects, advantages and capabilities of the present invention will become more apparent as the description proceeds, taken in conjunction with the accompanying drawings, in which.

DETAILED DESCRIPTION OF THE PREFERRED EMBODIMENT

Referring in detail to the drawings, and as a setting for the present invention, the preferred form of processing and transcribing system will be described with reference to the playback of ECG signals which are recorded on magnetic tape by a portable tape recorder. The portable tape recorder can be carried by the patient and has conventional electrodes taped to different parts of the body in a well-known manner so that the ambulatory patient can initiate recording as he pursues his normal day-to-day activities. The portable tape recorder as designated at R has a three-position switch which enables the patient to determine whether the recorder is to run continuously, is to sample at periodic time intervals or is to be placed on demand. In the "demand" setting D, the tape recorder will record signals from the electrodes as long as an "event" switch E is depressed; whereas, in the "sample" position S, the recorder will record for a predetermined interval such as ten seconds, stop recording for a predetermined time interval, such as, one minute, then record another ten-second interval. However, it is only in the "demand" position D that the recorder will remain on as long as the "event" switch E is activated. In either of the "continuous", "demand", or "sample" switch positions C, D, or S, respectively, the ECG signals are for example converted into a frequency division multiplex of the ECG signals and are supplemented by a time division multiplex of data signals which are interpositioned in the signal at periodic intervals to indicate for each preselected time period the switch setting, such as, whether the recorder was in the "event" position, the record count or aggregate time interval recorded, time of day and other information desired. The foregoing is provided only for the purpose of describing the nature of the FM and digital signal produced on tape. In accordance with conventional practice, while the recorder basically may be designed for a two-hour recording at a speed of 24 mm per second, the tape cassette employed may also be of a type which can be flipped over and a second two-hour recording made on the second track of the tape to provide the longest possible record over a given time period for subsequent diagnostic evaluation. The recorded tape cartridge or reel is inserted into the tape transport 13 and is returned to the beginning of the tape so that the FM signals and data bits when played back can be converted into traces of the ECG signals as originally recorded.

Figure 1:
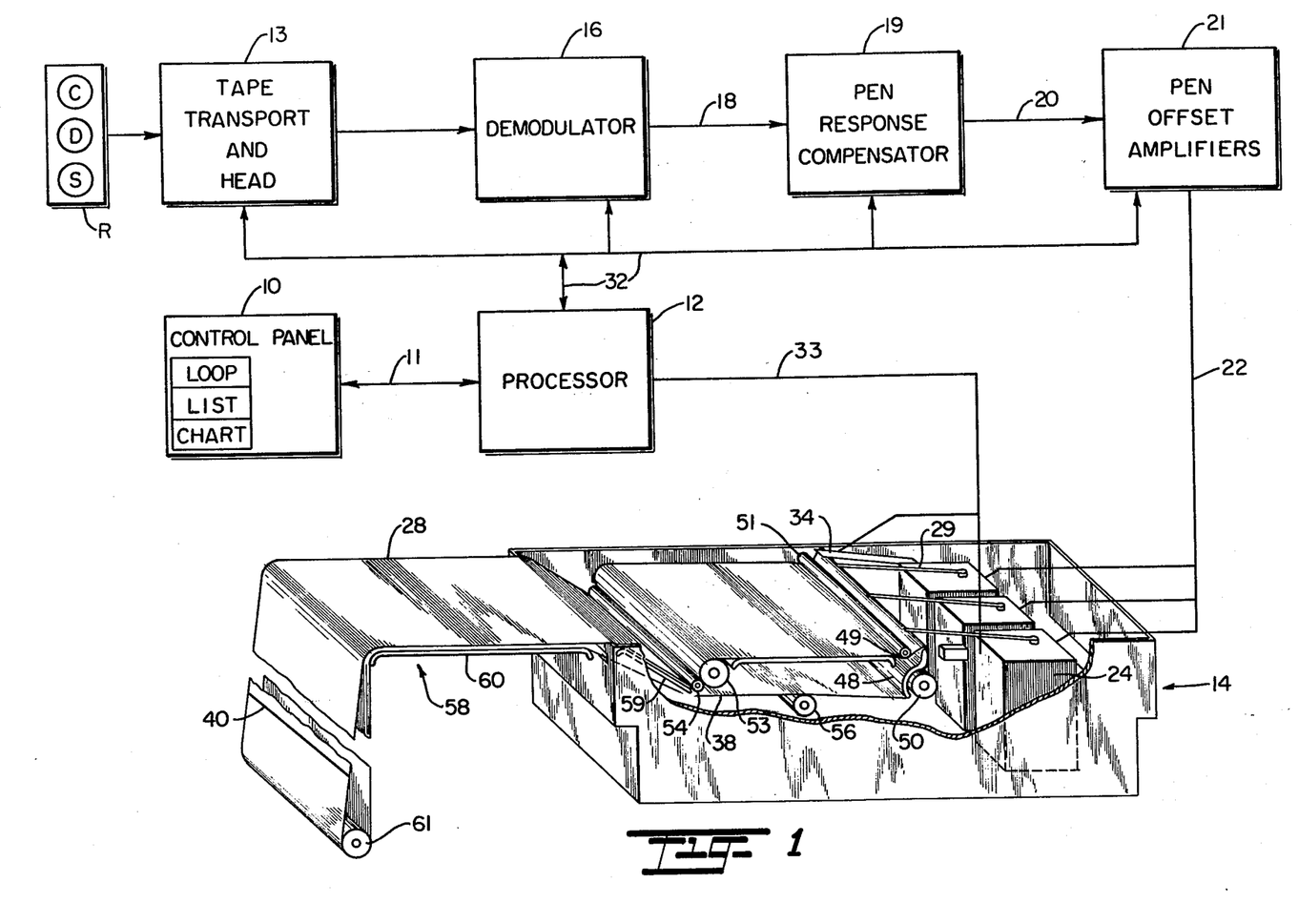
FIG. 1 is a block diagram of a system for processing and transcribing in accordance with the present invention and illustrating certain mechanical features of a chart paper drive unit when the system is in the loop mode.

As shown in FIG. 1, a control panel 10 is represented as having three switch positions to place the system either in the LOOP, LIST or CHART mode and which control signal is applied over an input line 11 to a microprocessor 12 to initiate recording and playback of the information at the desired speed. As hereinafter described in more detail, the LIST and CHART modes are utilized for the purpose of locating and playing back specific portions of the traces originally transcribed in compressed form in the LOOP mode. In the LOOP mode, the tape transport 13 is operated at a times ten playback speed and is initiated at the same time that the chart paper drive unit 14 is activated to drive the paper at a speed, for example, on the order of 25 mm per second. The FM and data signals on tape are therefore played back at a greatly increased speed ten times the recording speed under the control of the microprocessor and applied by the tape transport 13 to a demodulator circuit 16 which demodulates and converts the signals played back into a low voltage analog signal. In this way, a two-hour tape recording may be played back at ten times its normal recording speed, such as, 24 mm per second so as to be compressed into a twelve-minute recording. The demodulated signals are applied over line 18 to a pen response compensator 19 and then applied over line 20 to an amplifier circuit 21 which then transmits the signals over conductor 22 to one of a series of three galvanometer drive circuits 24 for activating write heads or pens P in the chart paper drive unit 14. In a conventional manner, the galvanometer pens P are responsive to the signals received from input line 22 to chart or record traces of the waveforms by scribing in a direction transversely of the movement of the chart paper 28 and, for this purpose, each pen includes a swivel arm 29 having a free end containing a stylus positioned directly above the writing surface of the chart paper 28. A control bus 32 extends from the microprocessor into the playback circuit as illustrated to order the processing of signals from the tape transport into the galvanometer pens; and another control line 33 extends from the microprocessor into a thermal print head represented at 34 to scribe additional data onto the writing surface of the chart paper and into a mark sensor 35 which will sense a synchronization mark on the chart paper in order to align the recording to be made with certain preprinted marks on the paper. Specifically the synchronization mark must be sensed by the mark sensor in order to initiate high speed playback of the information at the beginning of each trace to be formed on the chart paper.

Figure 3:
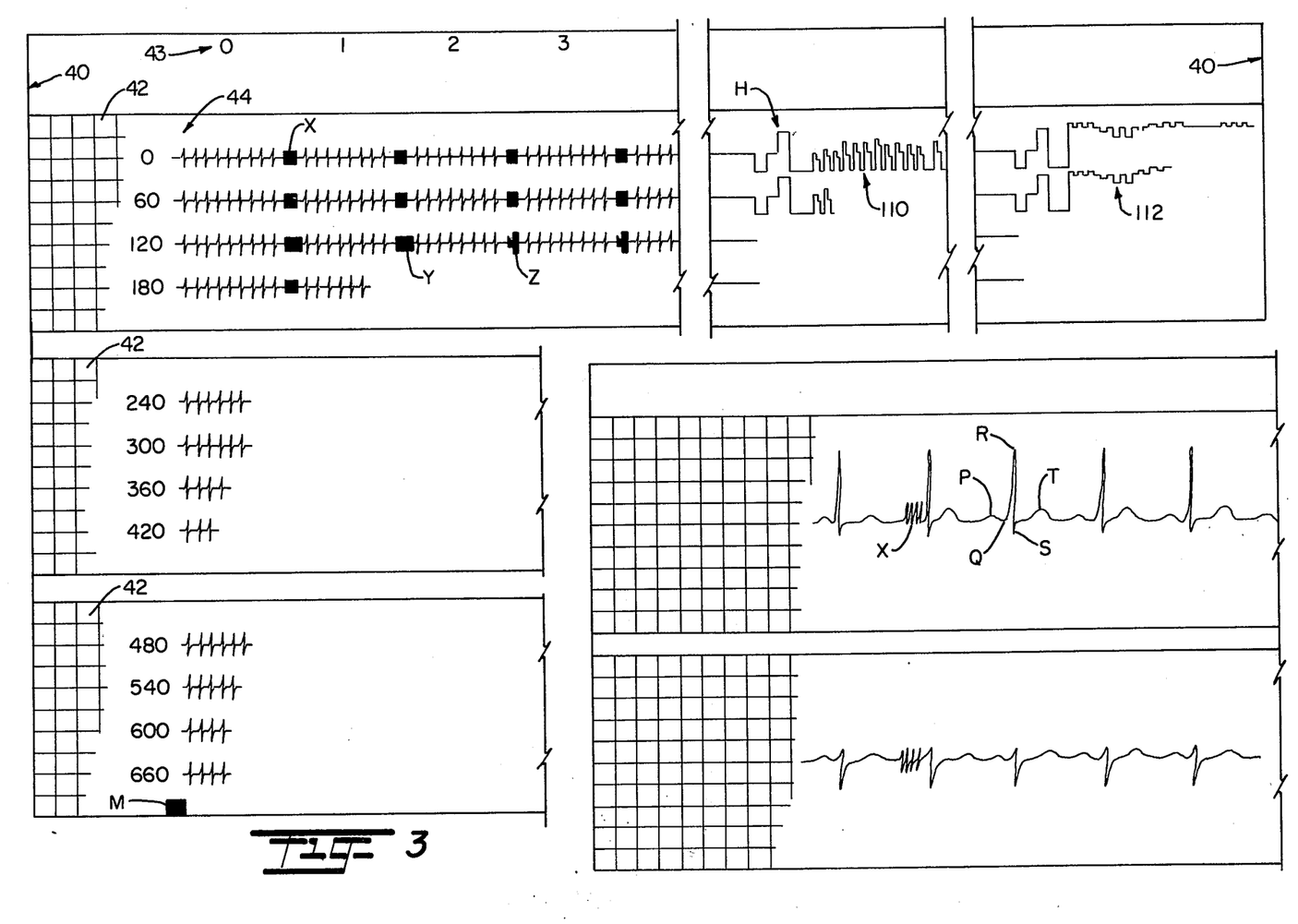
FIG. 3 is a somewhat fragmentary plan view illustrating the preferred form of chart paper together with graphical representations of ECG displays produced on the chart paper in accordance with the present invention.

In order to continuously drive the chart paper in a single direction and at a predetermined constant rate of speed and to record traces of the signals line-by-line proceeding in the same direction across the page while providing accurate correlation of the signals with respect to time and record count, the chart paper 28 is formed of an elongated, flexible strip or sheet of a preselected length and having opposite ends 40 joined together so as to define an endless loop or roll. As shown in FIG. 3, a writing surface 41 on the loop of paper is divided into a plurality of sectors or channels 42, the channels extending the substantial length of the loop and arranged in closely spaced coextensive relation to one another across the width of the loop. Each waveform trace or line is therefore scribed by a pen onto one of the channels by advancing the paper loop in a lengthwise direction past the pens so that each trace or line will extend lengthwise of a channel. A first set of numerical indicia represented at 43 are located at spaced intervals along the length of the paper loop so as to be arranged in ascending numerical order and to represent the discrete time intervals over which the ECG signals or waveform are transcribed. A second set of numerical indicia 44 are arranged in ascending numerical order laterally across the width of the paper loop and preferably across the ends of the channels or sectors adjacent to the starting point of each trace, the second set of numerical indicia representing the aggregate time intervals of the signals recorded and traced on the writing surface. Preferably each channel or sector 42 is divided by cross hatching into coordinate lines or grids in order to represent the amplitude and frequency of waveforms traced on the writing surface and each channel is of a width to permit tracing of a series of lines in laterally spaced relation to one another and extending lengthwise of the channel. By utilizing a series of channels or sectors corresponding to the number of pens P, each pen may be activated in succession to record a plurality of traces on each respective channel. As an illustration, for a two-hour tape recording which is played back at a speed which is increased by a multiple of ten, the entire recording can be played back in twelve minutes. The recording may then be divided into a predetermined number of lines corresponding to the length of the paper loop. Assuming that 16 cm. of compressed ECG data represents one minute of patient recording time, or 2.5 cm. represents ten seconds of ECG data, in order to break down the entire recording into twelve traces or lines of equal length, there being four lines transcribed in each channel or sector, the paper loop must be approximately 210 cm. in length, including some additional length for the copy of histograms at the end of each line. It is therefore important that the paper loop be handled and driven in such a way as to permit continuous advancement in the same direction past the galvanometer pens while continuous tension is applied to the paper without danger of misalignment or shifting of the paper.

In the preferred form of chart paper drive unit, a conventional chart recorder of the type which is designed for handling a paper supply roll for advancement of limited length or sheets of chart paper beneath the scribing pens is modified so as to adapt it for use with an endless paper loop or roll. One such conventional form of chart recorder is the American Optical Model No. 3355, manufactured by American Optical Corporation of Southbridge, Massachusetts, which is equipped with a set of three galvanometer pens P. A thermal print head 34 at one side of the pens and an optical sensor 35 at the opposite side are added as illustrated in FIG. 1. In addition, a print bar 48 has a relatively sharp upwardly directed edge 49 aligned directly beneath the free ends of the pen and cooperates with a tension roller 50 to define a guide path for the passage of paper upwardly from a supply roll, not shown, over the print bar and then advances beneath a guide roller 51 and onto and along a flat support plate 52. A friction drive roller 53 is located at the end of the support plate 52 opposite to the print bar 48 and in cooperation with a pinch roll 54 is operative to draw the paper off of the supply roll, not shown, and to advance it at a constant rate of speed past the scribing pens. In accordance with the present invention, the paper supply roll is removed from support shaft or arm 56 and the shaft 56 serves as a guide for the paper loop 38. A paper loop extension generally designated at 58 is made up of an inclined plate 59, a second horizontal table or support plate 60 disposed substantially in the plane of the plate 52, and a floating weight bar 61 is spaced beneath and beyond the end of the support plate 60 opposite to the drive roller 53. The floating weight 61 may hang freely in the closed end, represented at 39, of the paper loop 38 so as to maintain the proper tension or weight on the unused or closed portion of the paper loop. In this way, the weight is readily removable and is adaptable for use with different lengths of paper loops. In order to form the paper loop as hereinbefore described, one or both ends 40 of the paper loop may have contact cement or other adhesive applied thereto so that the sheet of paper may be first threaded into place as shown on the drive unit before joining the ends together, following which the paper loop is advanced to align the open end or portion 39' of the loop at a point beneath the scribing pens. In this relation, it will be noted that the excess or closed portion of the loop which is supported by the paper loop extension is folded or laid over the top of the support plate 60, then around and beneath the suspension weight 61 with the underside of the loop passing beneath the guide shaft 56, then advanced upwardly between the tension roller 50 and print bar 48. As a result, a minimum of drag or resistance is imposed on the advancement of the paper by the friction drive roller 54 while assuring proper lengthwise alignment of the paper as it is fed over and across the print bar and beneath the scribing pens. The entire recording process can take place automatically with no handling or adjustment of the paper loop required by the operator once playback is started, and playback and scribing on the writing surface of the paper can therefore proceed entirely under the control of the microprocessor.

Figure 2:
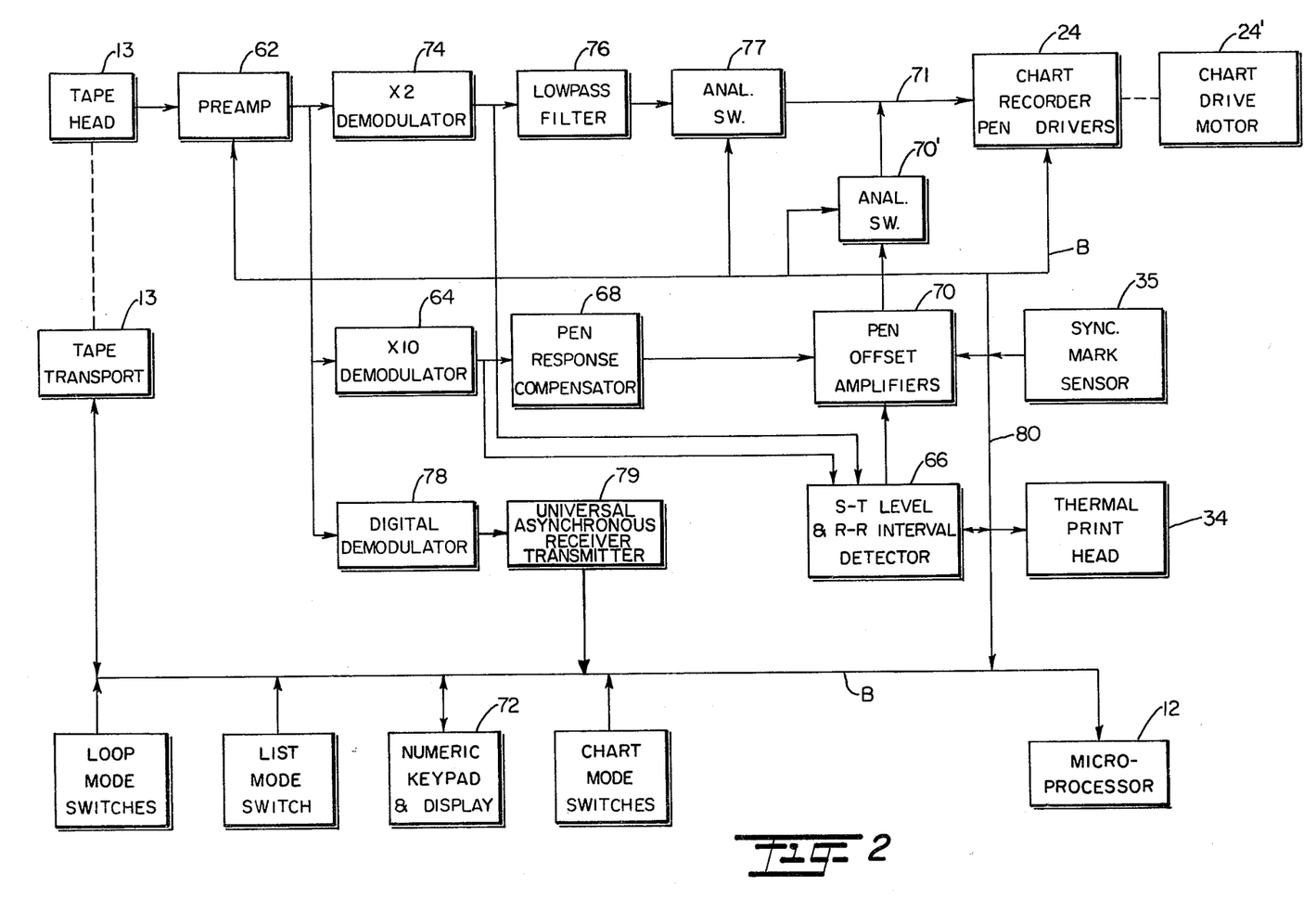
FIG. 2 is a block diagram illustrating further details of the system shown in FIG. 1.

Now considering in more detail the preferred form of playback circuit, as shown in FIG. 2, the ECG signals may be recorded as a single or multiplexed FM signal interrupted at equally spaced time intervals by a digital code which will designate the record count and mode of operation of the portable tape recorder during that time interval.

In the LOOP mode, a strip of paper is placed in the chart recorder and the ends of the strip secured together to form an endless loop. The LOOP mode switch on the control panel is depressed and the microprocessor 12 will rewind the tape and advance the paper loop to a start or synchronization mark M which is detected by the optical sensor 35 in the drive unit. The tape is then played back at the increased speed, here represented as ten times the original recording speed. The signal from the tape head 13 is amplified in the preamplifier circuit designated 62 and supplied to the "times ten" demodulator circuit 64 which will demodulate the signal into its original ECG waveform but in greatly compressed form. The output of the "times ten" demodulator is applied to the S-T level and R-R interval detector circuit 66. The R-R interval detector will detect the R-wave peak and store the R-R interval in a temporary register, while the S-T level detector will store the isoelectric point in the S-T level in digital form in temporary registers. The microprocessor will read each of these registers once per heartbeat and compute maximum and minimum heart rate and average S-T level for each ten-second or other selected time segment. These values are later transferred to the histogram memory which is then automatically recorded at the end of each line or trace through a digital-to-analog converter and analog output switch, not shown. The pen response compensator 68 also receives the output of the demodulator 64 which processes the signal to counter some of the degradation at the chart recorder pens all in a manner to be more specifically described with reference to FIGS. 4 and 5. The signal then passes through the pen offset amplifier circuit 70 through analog switch 70' to analog bus 71 into the chart recorder pen driver circuits 24. The analog output switch 70' controls the alignment or shifting of the pens P with respect to their respective channels so that for each pass of the paper loop, two of the pens will be aligned at the beginning of their respective channels and one pen will be aligned or shifted to record a trace on its respective channels, the synchronization or sequencing of pen movement being controlled by the microprocessor. The analog output switch 70' also contains a marker generator which will introduce a signal to illustrate a digital code X, Y or Z now to be described:

The digital code is taken off the carrier signal on tape and applied to digital demodulator circuit 78 and the universal asynchronous receiver/transmitter circuit 79. The circuit 79 will synchronize the information received from the demodulation 78. In turn, the processor will generate a tone burst based on the digital code received and transmit the burst over digital bus B to the pen drivers 24 for recording between each time segment, and will also transmit a signal of the record count to the thermal print head 34 for recording on the legend or margin of the chart paper in alignment with the digital code. Thus as illustrated in FIG. 3, different width markings represented by the digital code will be played back and transcribed on the writing surface by the processor to designate the mode of operation: A relatively thin marking X will indicate that the tape recorder was in a "continuous" mode; a relatively wide marking Y of the same height will designate a "sample" or "demand" recording; and a combination of two markings Z of different height will indicate that the recorder was in the "event" mode, or in other words that the event switch was on during a "continuous", "sample" or "demand" recording.

At the end of each complete line or trace consisting of 60 recording intervals, the tape transport heads are stopped to permit the microprocessor to read out from its histogram memory the S-T level and heart rate through a digital-to-analog converter, not shown, and analog output switch 70'. When the paper loop then reaches its starting point, the tape transport is restarted and the first pen is shifted to begin tracing the next line in succession in a channel. After completion of the last trace in the first channel, the first pen will be returned to its starting point and the second pen will be activated to record the next trace in succession on the second channel. Thus each time that a loop is completed by making one complete revolution of the paper roll, a recording pen will be offset or shifted a predetermined distance to record the next trace in succession and will continue until a predetermined number of traces have been produced in each channel. Again for a two-hour recording which has been compressed into twelve minutes for recording on an eighty inch roll, the twelve-minute recording may be divided into twelve traces each of one-minute duration with four traces being recorded in a line-over-line manner along the length of each channel or sector.

Upon completion of the recording in the LOOP mode, the tape transport and chart recorder automatically shut off and the chart paper loop is removed by separating along the spliced area. The completed paper loop will therefore contain two hours of information compressed into twelve minutes of patient recorded data time.

The LIST mode switch on the control panel 10 may be depressed after completion of the recording and, through an input keyboard 72, specific segments of interest on the completed recording can be requested for playback in a real time format. These are requested according to a combination of the time segment markings on the chart paper to pinpoint those areas to be examined in a real time format. The chart recorder is loaded with a standard roll of paper on a drum which, for example, may be supported on the shaft 56; and by depressing the CHART mode switch on the control panel the microprocessor will rerun the tape for the purpose of searching back to those segments to be printed or written out. At each desired segment, the chart recorder is run so that the ECG signal appears as shown at W in FIG. 3. The thermal print head 34 marks the chart paper with the record number of each ten-second interval and with the highest and lowest heart rate and the average S-T level for that ten-second record. Thus, when the CHART mode switch is depressed, the microprocessor will initiate a high speed search followed by real time printout of the desired data. In order to separate ten-second recording intervals from each other and to determine the mode of operation of the portable tape recorder as previously described the code markings between ten-second intervals will provide a ready means of reference in identification. In the CHART mode, preferably the ECG signals are routed through the "times two" demodulator circuit 74 through low pass filters 76 which can be used at the operator's discretion to reduce noise on the printout. These signals are then applied via analog output switch 77 onto the ECG bus 71 and the chart recorder pen drivers 24; and the chart motor drive 24' also is run at twice its normal speed so as to result in the production of traces in a real time format.

Figure 4:
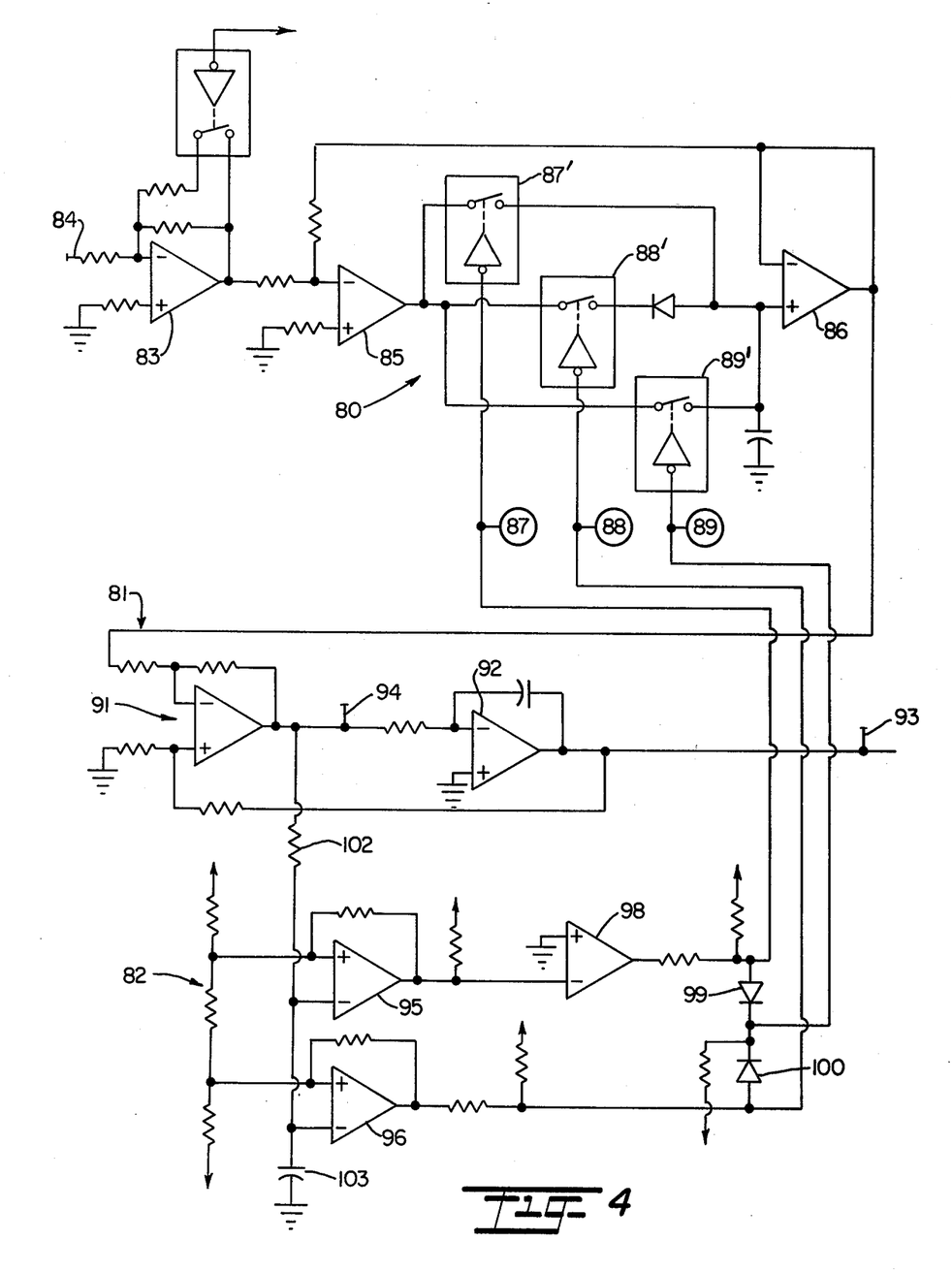
FIG. 4 is a circuit diagram showing a pulse stretcher portion of the playback circuit, in accordance with the present invention.

In recording or displaying traces of electrical pattern or waveform of the cardiac cycle as illustrated in FIG. 3, it is important for the purpose of diagnostic evaluation that the principal waves or deflections be readily discernible by the diagnostician in order that specific segments of interest can be pinpointed for more detailed evaluation. In recording the five principal waves known as P, Q, R, S and T, the scribing pens will not accurately track the narrow QRS complex when the data is being played back at greatly increased rates of speed unless means are provided for stretching or elongating the complex in time without affecting the rest of the waveform and particularly the amplitude of the principal waves. As illustrated the QRS complex is comprised of a downward deflection referred to as the Q wave, a greater upward deflection referred to as the R wave and a second downward deflection referred to as the S wave all as designated in FIG. 3. It is therefore the function of the pen response compensator 58 which includes a pulse stretcher circuit to stretch the waveform produced of the QRS complex for the purpose of recording without retarding or reducing the speed of playback. As shown in FIG. 4, the pulse stretcher comprises a peak detector represented at 80 in cooperation with a slew rate limitor circuit 81 and slew rate detector circuit 82. In the peak detector circuit, an operational amplifier 83 inverts the input signal from the times ten demodulator circuit which is applied over input line 84 and reduces its amplitude to a level on the order of one-half of the input signal. The operational amplifiers 85 and 86 together define a track-and-hold peak detector whose functions are controlled by analog switches 87, 88 and 89 each of which includes switch component 87', 88' and 89', respectively. The output line 90 of the peak detector circuit is applied to the slew rate limitor circuit 81 which has a differential amplifier 91 driving an integrator 92, the output of the former going to zero when the output over line 90 matches the integrator output over line 93. When the differential amplifier output on line 94 saturates positive or negative, the integrator 92 will slew at a fixed rate, such as, for instance 200 volts per second. The voltage on line 94 is always proportional to the slew rate over line 93. In turn, the slew rate detector circuit includes two comparators 95 and 96 which examine the slew rate output over line 94. A third comparator 98 is used as an inverter, and a pair of diodes 99 and 100 form an OR gate. Generally, as long as the input waveform slews at a rate less than the fixed rate of the integrator, the output over line 90 will closely track the input. However, as soon as the slew rate of the input exceeds the fixed rate, the peak detector will track the input waveform and hold the highest voltage reached. The slew rate detector incorporates a time delay formed by resistor 102 and capacitor 103 to allow the slew rate limiter circuit to catch up to the input thereby increasing the stability of the circuit.

As long as the peak detector circuit 80 is not slew rate limited, its output tracks the input; if a fast positive peak appears at the input, the peak detector switches into a track-positive-peak mode of operation and will hold the highest voltage applied over line 84 until the voltage over line 90 reaches the same level. If at this time the voltage is lower than the voltage over output line 93, the output will immediately go into a negative going slew rate and the analog switches will switch into a track-negative. When the slew rate limited output finally catches up with the input over line 90, it will track until the next peak occurs with a high slew rate. The comparative waveforms at different internal points in the pulse stretcher circuit are illustrated in FIG. 5.

Figure 5:
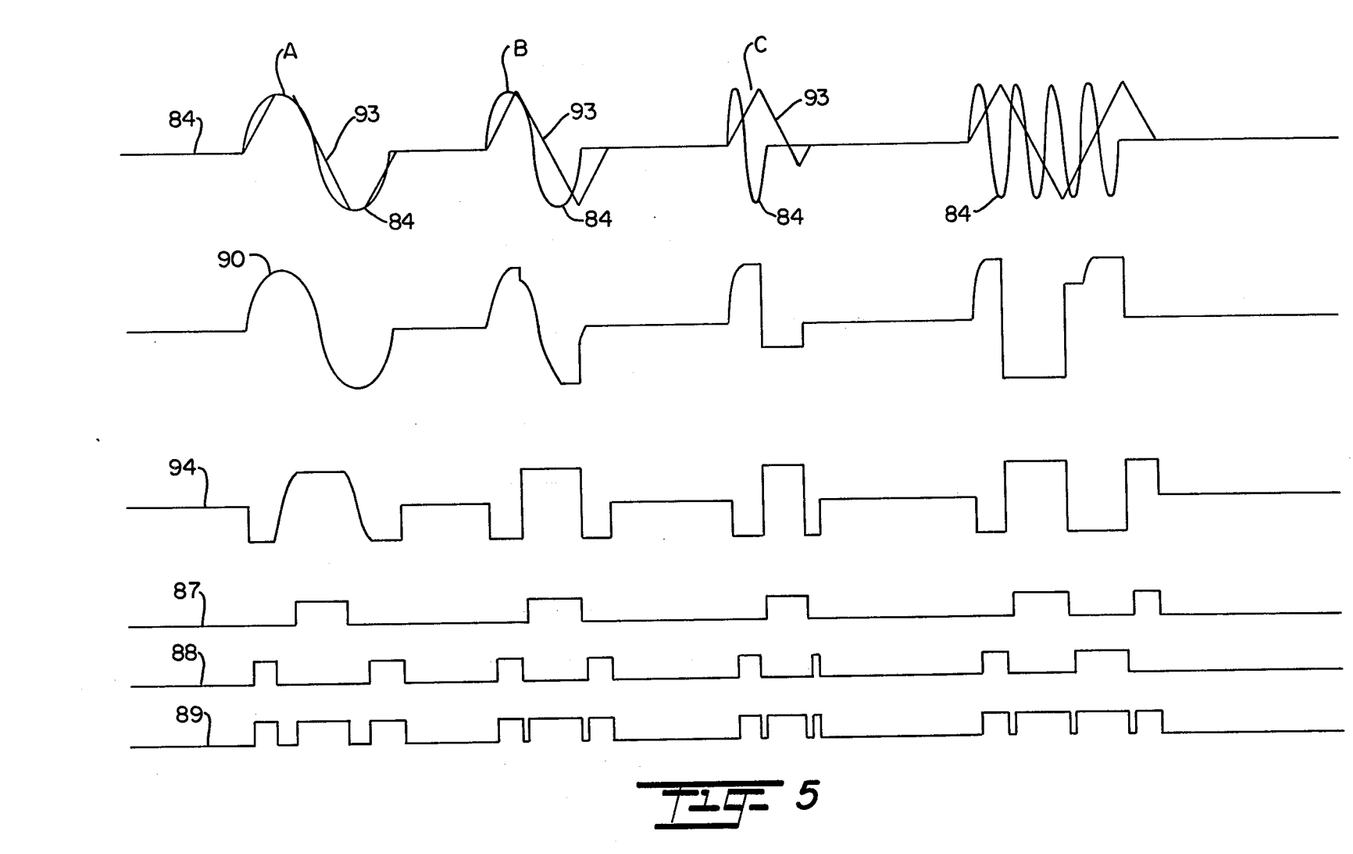
FIG. 5 is a timing diagram illustrating the waveforms produced by the pulse stretcher portion of the circuitry shown in FIG. 4.

An examination of FIG. 5 reveals the effect of the pulse stretcher circuit on the output waveforms as applied over line 93 when superimposed over the input waveform as applied over input line 84. In A the peak is just fast enough to start the slew rate limiting, causing straight line segments on the output line 93. In B the input frequency has been increased so that the pulse stretcher will lengthen the pulse while preserving the amplitude. In C the input pulse is so short that the negative peak occurs before the output has reached the positive peak so as to reduce the amplitude of the negative output peak.

Referring once again to FIG. 3, each line or trace of waveforms along the length of each channel is followed by histograms H of the information recorded over that time segment. The first histogram illustrates or represents at 110 the maximum and minimum heart rates in beats per minute for each of the time segment intervals. Assuming that sixty ten-second intervals have been compressed and recorded into sixty one-second records, the maximum and minimum heart rate of that interval will be displayed in the first histogram 110. The second histogram 112 displays the average S-T level of the waveform recorded along each trace. At the conclusion of the second histogram, one complete rotation or revolution of the chart paper loop will have occurred. Thereafter, the recording pen will be shifted laterally a predetermined distance under the control of the pen offset amplifier circuit in preparation for recording the next trace in succession, and the operation will be repeated for each recording pen to produce a number of longitudinally extending, parallel coextensive traces in each channel in succession.

As previously described, once the entire recording has been completed, the ends 40 of the paper loop are separated and the recording removed from the chart recorder and a standard roll or sheet may then be placed in the recorder as a preliminary to operation in the LIST and CHART modes as described. In recording segments of interest during the CHART mode, the thermal print head will print along the legend of the writing surface record identification numbers to identify the time segments being played back in a real time format and recorded on the chart paper together with other information. For example, it may print out at the end of each segment recorded the actual values of the highest and lowest heart rate and the average S-T level for that interval.

While the present invention has been described specifically in connection with the processing and displaying of FM signals which include a reference carrier signal, its ready conformability for processing other types of signals will be readily appreciated. Thus for instance, the signal as recorded on magnetic tape may comprise a frequency division multiplex signal with a reference carrier or header bit data interrupting that signal at predetermined time intervals. The demodulated circuit may then be designed to divide the multiplex signal into two different channels and the microprocessor will then select which of the signals is to be recorded or transcribed onto the writing surface. Transcription of these signals in multiples of real time recording then provides the physician with a preliminary means of evaluating his patient over an extended time interval. Accordingly, the length of the endless loop may be varied according to the total recording time. In this connection, the chart paper drive system is readily conformable for handling different lengths of endless loops and, as described, is readily interchangeable for use either with a standard roll of chart paper or an endless loop. It is therefore to be understood that various modifications and changes may be made in the preferred embodiment of invention as described without departing from the spirit and scope thereof as defined by the appended claims.

What is claimed is:

1. In a compressed data recording system including sensing means for generating electrical signals representing the ECG level of the patient, playback means responsive to the signals generated to reproduce waveforms of said signals at a predetermined rate of speed, a plurality of write heads, a movable recording medium associated with said write heads for recording said waveforms, and means for moving said recording medium past said write heads, said write heads being disposed at spaced intervals transversely of the movement of said recording medium past said write heads, the improvement comprising:

said recording medium defined by an elongated flexible strip of recording material having its ends joined together to form an endless loop of material; a writing surface on said loop of material divided into a plurality of sectors, each of said sectors extending the substantial length of said loop and arranged in closely spaced, coextensive relation to one another, each sector providing a plurality of trace-recording channels thereacross for the graphical representation of said waveforms by each write head along the substantial length of said respective channel, the number of sectors corresponding to the number of write heads; and means for aligning each write head adjacent to one lateral edge of an associated sector, activating means for activating each write head in succession to form a graphical representation of the waveform reproduced by said playback means lengthwise of each sector as said recording medium is advanced past said write heads, shift means for laterally shifting said activated write head each time that said activated write head traverses and records the trace along the substantial length of its associated sector, each write head being activated in response to the recording of a predetermined number of traces in laterally spaced relation to one another by a preceding adjacent write head across said adjacent write head's associated sector.

2. In a compressed data recording system according to claim 1, said trace-recording medium containing a first set of numerical indicia arranged in ascending numerical order extending the length of said writing surface representing discrete time intervals over which an ECG waveform is to be recorded.

3. In a compressed data recording system according to claim 2, said trace-recording medium containing a second set of numerical indicia arranged in ascending numerical order across the width of said sectors and representing the aggregate time intervals of the preceding waveforms traced on said sectors.

4. In a compressed data recording system according to claim 2, including a synchronization mark on said writing surface to correlate the beginning of each channel to be recorded with the first set of numerical data.

5. In a compressed data recording system according to claim 1, each sector divided into coordinate grids to represent the amplitude and frequency of the waveforms traced, and each sector being of a width permitting the tracing of a series of waveforms across the width thereof.

6. A data playback and recording system including a recorder and a transcriber adapted for the graphical representation of ECG waveforms and the like obtained from ECG signals of a patient in modulated form over an extended time period and wherein a plurality of scribing elements are positioned in confronting relation to a print bar, the combination therewith comprising:

a recording medium defined by an elongated flexible strip of material in the form of an endless loop and provided with a writing surface thereon;

a recording medium advancement means for advancing said recording medium past said scribing elements, said recording medium advancement means including loop support means adapted to support said endless loop for advancement across said print bar and drive roller means to draw said loop in a lengthwise direction across said print bar;

means for sensing said ECG signals and producing said ECG signals as electrical signals at a speed greater than real time; and circuit means responsive to said electrical signals to produce demodulated signals having the same waveform as said ECG signals, drive means to activate each scribing element in succession for transcribing a graphical representation of said demodulated signals along the length of said writing surface, in greater than real time, detector means for detecting the slew rate of said demodulated signals, and pulse stretcher means associated with said detector means and operative to increase the width of the waveform of said demodulated signals from which said graphical representations are derived when demodulated signals having a slew rate greater than a predetermined value are detected.

7. A data playback and recording system according to claim 6 wherein the recorder is operative in a selected one of a plurality of modes of operation and wherein ECG signals obtained including digital control signals generated independent of said data and containing mode information indicative of said selected one of said modes of operation, and said circuit means includes means for demodulating said digital control signals, and processor means for transmitting said demodulated digital control signals to said drive means for transcribing in correlation with and together with said ECG waveforms.

8. A chart recording unit adapted for the graphical representation of ECG waveforms in which ECG signals are produced as electrical signals at a speed greater than real time and said chart recording unit includes a print bar and a scribing element positioned in confronting relation to said print bar, the combination therewith comprising:

a recording medium defined by an elongated flexible strip of material in the form of a continuous loop having a writing surface thereon;

loop support means for supporting said endless loop, said loop support means including a print bar, a plurality of guide rollers, and a support table, said print bar adapted for extension into the interior of said loop and supporting an interior surface portion of said loop with said loop disposed in surrounding relation to said print bar, said guide rollers journaled on spaced parallel axes with a portion of said loop being threaded around said guide rollers, said support table mounted adjacent said guide rollers opposite said print bar and for supporting an exterior surface portion of said loop, a portion of said loop extending over an edge of said support table opposite said guide rollers in freely hanging relation thereto;

guide roller drive means associated with one of said guide rollers for rotating said one of said guide rollers whereby said writing surface is advanced in a lengthwise direction past said scribing element; and circuit means responsive to said electrical signals to produce demodulated signals having the same waveform as said ECG signals, drive means to activate said scribing element for transcribing a graphical representation of said demodulated signals along the length of said writing surface in greater than real time, detector means for detecting the slew rate of said demodulated signals, and pulse stretcher means associated with said detector means and operative to increase the width of the waveform of said demodulated signals from which said graphical representations are derived when demodulated signals having a slew rate greater than a predetermined level are derived.

9. A chart recording unit according to claim 8, said guide roller drive means being disposed in spaced relation to said print bar in a direction toward said support table and including a horizontal support plate being interpositioned between said guide rollers and said print bar.

10. A chart recording unit according to claim 9, said support table aligned with said support plate in a common plane.

11. The method of processing and displaying ECG waveforms representing the ECG signals of an ambulatory patient over a long term interval stored in the form of retrievable modulated signals, comprising the steps of:

storing said ECG signals as modulated signals at a given rate;

retrieving said stored ECG signals and producing first demodulated signals having demodulated waveforms at a rate of speed which is a multiple of said given rate;

transcribing discontinuous traces of the demodulated waveforms in parallel rows along the length of a writing surface at a time rate correlated with time segment markings along the length of said writing surface;

detecting the slew rate of said first demodulated signals and elongating the waveforms of the first demodulated signals when the slew rate of said first demodulated signals exceeds a predetermined level; and expanding selected portions of said traces by producing second demodulated signals corresponding to said given rate and re-transcribing said second demodulated signals.

12. The method according to claim 11 wherein said step of storing said ECG signals includes storing said ECG waveforms in a selected one of a plurality of modes of operation further including the step of producing digital control signals at equally spaced time intervals between the demodulated waveforms of said first demodulated signals for registering the mode of operation of said ECG storing step.

* * * * *